US010517470B2

(12) United States Patent
Hopkins, Jr.

(10) Patent No.: US 10,517,470 B2
(45) Date of Patent: Dec. 31, 2019

(54) OPTICAL INSTRUMENT AND ARTICULATING IMAGE SENSING APPARATUS THEREFOR

(71) Applicant: KARL STORZ Endovision, Inc., Charlton, MA (US)

(72) Inventor: Vernon Hopkins, Jr., Worcester, MA (US)

(73) Assignee: KARL STORZ Endovision, Inc., Charlton, MA (US)

( * ) Notice: Subject to any disclaimer, the term of this patent is extended or adjusted under 35 U.S.C. 154(b) by 426 days.

(21) Appl. No.: 15/154,884

(22) Filed: May 13, 2016

(65) Prior Publication Data

US 2017/0325671 A1  Nov. 16, 2017

(51) Int. Cl.
*A61B 1/05* (2006.01)
*A61B 1/00* (2006.01)
(Continued)

(52) U.S. Cl.
CPC .............. *A61B 1/05* (2013.01); *A61B 1/0008* (2013.01); *A61B 1/00183* (2013.01);
(Continued)

(58) Field of Classification Search
CPC ..... A61B 1/05; A61B 1/0008; A61B 1/00183; A61B 1/045; A61B 1/051; A61B 1/0623; A61B 1/0676; G02B 23/2476
(Continued)

(56) References Cited

U.S. PATENT DOCUMENTS 3,856,000 A  12/1974 Chikama
3,896,793 A   7/1975 Mitsui et al.
(Continued)

FOREIGN PATENT DOCUMENTS

DE  102012206963 A1  10/2012
EP       1348371 B1   1/2013
JP    H07327916 A  12/1995

OTHER PUBLICATIONS

European Search Report, Application No. EP 17 00 0749, dated Oct. 17, 2017.

*Primary Examiner* — Timothy J Neal
*Assistant Examiner* — William B Chou
(74) *Attorney, Agent, or Firm* — The Culbertson Group, P.C.; Russell D. Culbertson

(57) ABSTRACT

An imaging apparatus is adapted for use in an optical instrument having an elongated shaft with a transparent distal end portion. The imaging apparatus includes and image sensor assembly, a first articulating structure, and a second articulating structure mounted on the first articulating structure. First and second lateral side support structures at the lateral sides of the image sensor assembly are each mounted on the second articulating structure so as to position the image sensor assembly in an operating position in the instrument transparent end portion. The connection to the second articulating structure allows an articulation of the image sensor assembly about a lateral articulation axis extending transverse to the longitudinal axis of the shaft distal end portion. This lateral articulation is in addition to the ability of the first articulating structure to rotate about the longitudinal axis of the shaft distal end portion.

18 Claims, 5 Drawing Sheets

(51) Int. Cl.
*A61B 1/045* (2006.01)
*A61B 1/06* (2006.01)
*G02B 23/24* (2006.01)

(52) U.S. Cl.
CPC .............. *A61B 1/045* (2013.01); *A61B 1/051* (2013.01); *A61B 1/0623* (2013.01); *A61B 1/0676* (2013.01); *G02B 23/2484* (2013.01)

(58) Field of Classification Search
USPC ....... 600/109, 112, 117, 129, 160, 170, 171, 600/173, 174, 176, 177, 178
See application file for complete search history.

(56) References Cited

U.S. PATENT DOCUMENTS

| | | | |
|---|---|---|---|
| 6,364,830 B1 | 4/2002 | Durell | |
| 6,371,909 B1 | 4/2002 | Hoeg et al. | |
| 6,428,470 B1 | 8/2002 | Thompson | |
| 6,428,471 B1 | 8/2002 | Durell, Jr. | |
| 6,560,013 B1 | 5/2003 | Ramsbottom | |
| 6,638,216 B1 * | 10/2003 | Durell ................ | A61B 1/00165 600/129 |
| 6,916,286 B2 * | 7/2005 | Kazakevich ....... | A61B 1/00105 600/129 |
| 6,929,603 B2 | 8/2005 | Durell | |
| 7,344,494 B2 | 3/2008 | Hoeg et al. | |
| 7,374,533 B2 | 5/2008 | Hoeg et al. | |
| 8,485,968 B2 | 7/2013 | Weimer et al. | |
| 8,702,597 B2 * | 4/2014 | Iddan ................ | A61B 1/00094 600/167 |
| 8,852,086 B2 * | 10/2014 | Pauli ................ | A61B 1/00066 600/170 |
| 8,870,758 B2 | 10/2014 | Dahmen et al. | |
| 9,028,399 B2 | 5/2015 | Irion | |
| 9,456,735 B2 * | 10/2016 | Hrayr ................ | A61B 1/00183 |
| 9,649,016 B2 * | 5/2017 | Wada ................ | A61B 1/00183 |
| 9,763,563 B2 * | 9/2017 | Hoeg ................ | A61B 1/00181 |
| 9,877,638 B2 * | 1/2018 | Buerk ................ | A61B 1/00183 |
| 9,907,457 B2 * | 3/2018 | Grant ................ | A61B 1/00183 |
| 2005/0234296 A1 * | 10/2005 | Saadat ................ | A61B 1/0008 600/129 |
| 2006/0129032 A1 * | 6/2006 | Durell ................ | A61B 1/00165 600/173 |
| 2007/0055103 A1 | 3/2007 | Hoefig et al. | |
| 2012/0078049 A1 | 3/2012 | Pauli et al. | |
| 2014/0012080 A1 | 1/2014 | Wada et al. | |
| 2014/0142385 A1 | 5/2014 | Dahmen | |
| 2015/0238068 A1 | 8/2015 | Rose et al. | |
| 2015/0359420 A1 | 12/2015 | Hatase et al. | |

* cited by examiner

OPTICAL INSTRUMENT AND ARTICULATING IMAGE SENSING APPARATUS THEREFOR

TECHNICAL FIELD OF THE INVENTION

The invention relates to optical instruments such as endoscopes and borescopes having an image sensor assembly at the distal end of the instrument shaft. More particularly, the invention relates to image sensing systems that can produce an image from a wide range of orientations within the distal end of the instrument shaft, and to optical instruments incorporating such image sensing systems.

BACKGROUND OF THE INVENTION

Instruments such as endoscopes and borescopes are used to allow a visual inspection of locations which are not readily accessible. For example, endoscopes are used in medical applications to provide a view of an area within a patient's body. Whether employed for medical or other applications, the instrument typically includes an elongated shaft of relatively small diameter extending from a handle to a distal end. An imaging or viewing arrangement is included with the instrument to allow a user to obtain a view from the shaft distal end. This arrangement may include a system of lenses and a light conduit through the shaft to direct an image from the distal end to an eyepiece associated with the instrument handle. Alternatively, the imaging or viewing arrangement may include an electronic imaging device at the distal end of the instrument shaft. Such an electronic imaging device collects image data and communicates that data through the shaft and handle ultimately to a processing system that assembles the data to produce an image displayed on a suitable display device.

Depending upon the procedure for which the instrument is used, it may be necessary for the operator to view a relatively large area, or view a relatively small area from different angles. In a medical procedure for example, the operator may desire to view a location which is larger than the field of view of the imaging collecting arrangement of the endoscope or view a location from different angles. In these situations it has been necessary for the endoscope operator to move the distal end of the endoscope in an effort to provide the desired views, and sometimes move the distal end repeatedly in given area.

Endoscopes have been developed to give the operator the ability to adjust viewing angle. U.S. Patent Application Publication No. 2015/0238068 discloses an endoscope having an objective lens and prism that is mounted on a pivotable structure at the distal end of the endoscope. This endoscope, however, allows rotation to only one side of the device. Thus the endoscope had to be repositioned in the area of the procedure in order to view a location on the opposite side of the endoscope shaft. U.S. Patent Application Publication No. 2014/0012080 shows another endoscope with an image collecting part which may be tilted to one side of the endoscope at the distal end. This arrangement also requires the endoscope distal end to be repositioned to obtain views of areas on the opposite side of the endoscope shaft (that is, opposite the side to which the image collecting device is tilted at a given point in time).

U.S. Pat. No. 6,371,909 discloses an endoscope having an imaging assembly mounted in the distal end of the endoscope so as to allow articulation about two axes. This two-axis articulation facilitates different viewing angles through a transparent cover at the distal end of the endoscope. The articulating arrangement disclosed in U.S. Pat. No. 6,371,909, however, greatly constrained the nature and size of the imaging device which could be employed for a given diameter endoscope distal end. Also, the distal end of the endoscope in U.S. Pat. No. 6,371,909 had to be repositioned to provide a view of any area other than the area at the far distal tip of the endoscope shaft.

There remains a need in the art to provide an optical instrument such as an endoscope or borescope that allows the imaging device to be adjusted so that different views can be obtained without having to move the instrument distal end, or at least limiting the amount to which the distal end must be moved in a given procedure.

SUMMARY OF THE INVENTION

It is an object of the invention to provide an optical instrument such as an endoscope or borescope having an image sensor which can be articulated within the instrument shaft about both a longitudinal axis and a lateral articulation axis. The invention also encompasses an imaging apparatus that facilitates this articulation.

An imaging apparatus according to one aspect of the present invention is adapted for use in an optical instrument such as an endoscope or borescope having an elongated shaft with a transparent distal end portion. Such an optical instrument will be referred to in this disclosure and the accompanying claims simply as an "instrument," and this term is intended to encompass endoscopes, borescopes, and similar optical instruments.

The imaging apparatus according to this aspect of the invention includes an image sensor assembly, a first articulating structure, and a second articulating structure mounted on the first articulating structure. A first lateral side support structure is located at a first lateral side of the image sensor assembly, and a second lateral side support structure is located at a second lateral side of the image sensor assembly. These first and second lateral side support structures are each mounted on the second articulating structure so as to position the image sensor assembly in the instrument transparent distal end portion when the imaging apparatus is in an operating position within the instrument shaft. The connection between the lateral side support structures and the second articulating structure allows an articulation of the image sensor assembly about a lateral articulation axis extending transverse to the longitudinal axis of the shaft distal end portion. This lateral articulation is in addition to the ability of the first articulating structure to rotate about the shaft distal end portion longitudinal axis.

The combination of the image sensor assembly mounted on the second articulating structure, which is in turn mounted on the first articulating structure, facilitates the articulation of the image sensor assembly within the instrument shaft about two axes. The articulation about these two axes allows the image sensor assembly to be positioned within the instrument so that its image sensing axis is directed in any direction a full 360° about the shaft distal end portion longitudinal axis and also laterally about the lateral articulation axis preferably at least 90°, and even further in some embodiments as will be described below. Thus when the imaging apparatus is mounted in an instrument, the instrument is capable of providing an overall field of view over a relatively large area without having to move the distal end portion of the instrument.

When the imaging apparatus is mounted in the operating position within an instrument shaft, an articulation control assembly may be used to control the articulation of the image sensor assembly. In particular, the articulation control assembly may be used to control the rotation of the first articulating structure, and thus the image sensor assembly, about the distal end portion longitudinal axis. The articulation control assembly may also be used to control the articulation of the image sensor assembly about the lateral articulation axis. As will be described below in connection with the representative embodiments, any suitable arrangement may be employed in the articulation control assembly to effect the desired movement of the image sensor assembly, including various types of motors and mechanical linkages to the image sensor assembly.

The first articulating structure in some implementations of an imaging apparatus according to the invention may comprise an elongated tube adapted to be positioned within the distal end portion of the instrument shaft with the longitudinal axis of the tube aligning with the longitudinal axis of the distal end portion of the instrument shaft. In these implementations, the elongated tube mounted in the operating position within the instrument shaft may terminate short of the distal end of the instrument shaft provided the image sensor assembly is positioned appropriately within the transparent end portion of the shaft. Otherwise, the elongated tube may include a distal end section which is adapted to extend distally past the image sensor assembly in the instrument shaft when the imaging apparatus is mounted in the operating position. In these embodiments the distal end section of the elongated tube includes a transparent part over at least a field of view range for the image sensor assembly about the lateral articulation axis. In either case, an elongated tube comprising the first articulating structure may include a proximal end adapted to extend to a handle of the instrument when the imaging apparatus is mounted in the operating position. The proximal end of the tube may be connected to a suitable rotation control device associated with the instrument handle to facilitate control of the articulation about the distal end portion longitudinal axis.

In some implementations of the articulating imaging apparatus, one or more light sources are mounted on the image sensor assembly. This placement of light sources for the image sensor assembly ensures proper illumination is available for imaging regardless of the orientation of the image sensor assembly within the instrument shaft.

In addition to facilitating articulation about the distal end portion longitudinal axis and the lateral articulation axis, some implementations of the imaging apparatus allow the image sensor assembly to be moved longitudinally within the shaft distal end portion. This longitudinal movement increases overall field of view for the image sensor assembly about the instrument distal end portion.

Implementations of the second articulating structure (which facilitates articulation about the lateral articulation axis) may include a pivoting structure to facilitate the lateral articulation. In these implementations the lateral side support structures may each include a pivot element positioned at the respective lateral side of the image sensor assembly and aligned along the lateral articulation axis. The second articulating structure may then include first and second pivot bases mounted on the first articulating structure and each connected with a respective pivot element to allow rotation of the pivot elements about the lateral articulation axis. The pivot bases or pivot elements in these pivot structure-type embodiments may be configured to allow longitudinal movement along the longitudinal axis of the instrument distal end portion when the imaging apparatus is in the operating position.

Alternatively to the pivot structure-type embodiments, the second articulating structure may include a track-based structure. In these track-based embodiments, each of the two lateral side support structures includes fore and aft projections positioned at the respective lateral side of the image sensor assembly. The fore and aft projections are aligned, respectively, along fore and aft axes in these embodiments and project past a plane aligned with and extending perpendicular to the respective lateral side to be received in a respective track. Each track includes a transverse section and a longitudinal section connected together by a curved section. The transverse sections each extend transverse to the longitudinal axis of the distal end portion of while the longitudinal sections each extend parallel to the longitudinal axis of the instrument distal end portion when the imaging structure is in the operating position. This track-based arrangement allows the image sensor assembly to move to different positions along the track, which, due to the transverse and longitudinal sections, places the image sensor assembly at different angular orientations about the lateral articulation axis.

In embodiments including a track-based structure for facilitating articulation of the image sensor assembly about the lateral articulation axis, each track may include an inclined section at a bottom end of the respective longitudinal section. The inclined sections are each inclined so that they define a deviation greater than 90° with respect to the transverse sections. Thus the inclined sections of the tracks allow the image sensor assembly to be positioned with the image sensing axis extending somewhat backwards along the instrument shaft, away from the shaft distal end.

These and other advantages and features of the invention will be apparent from the following description of representative embodiments, considered along with the accompanying drawings.

DESCRIPTION OF REPRESENTATIVE EMBODIMENTS

Figure 1:
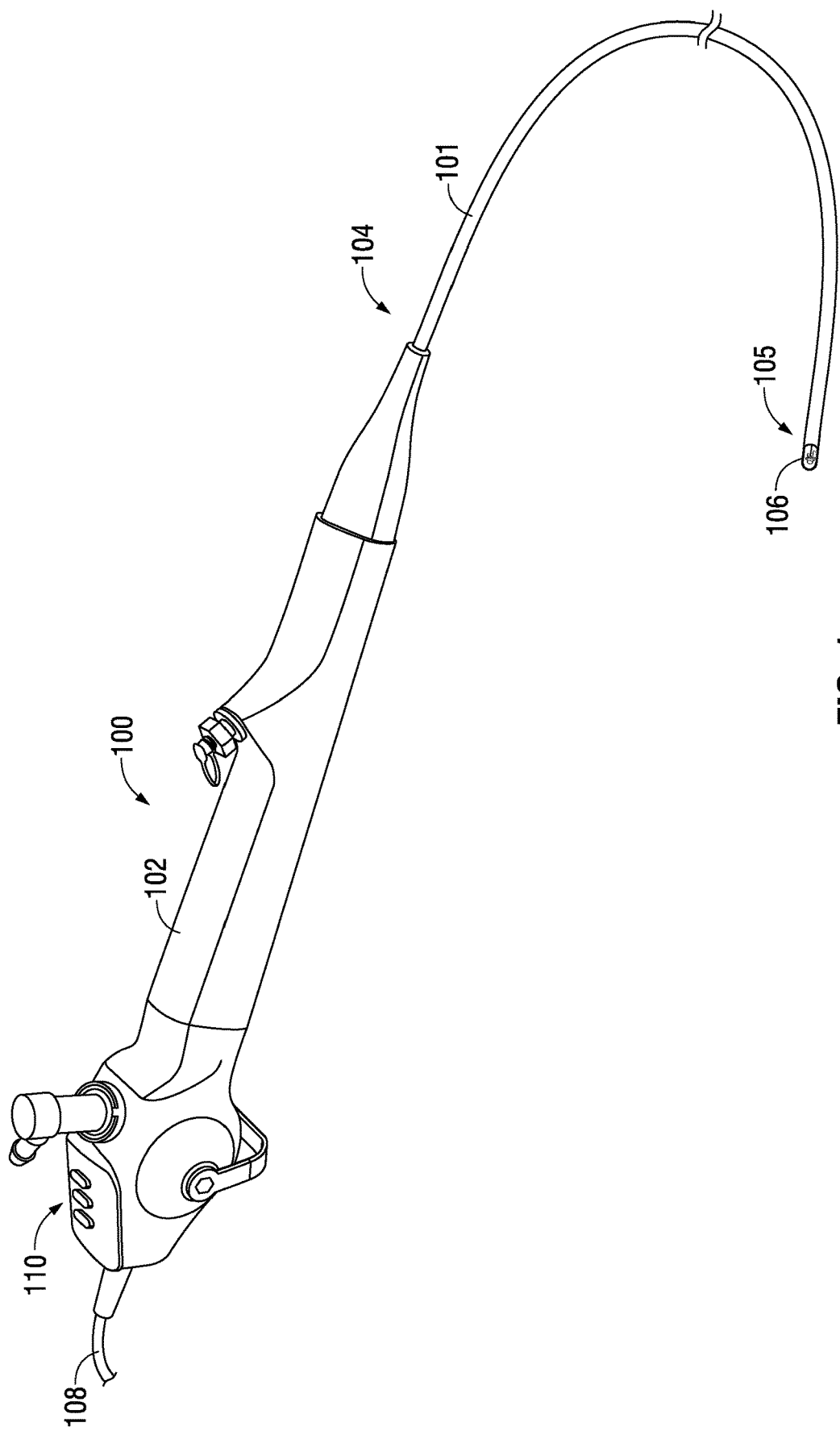
FIG. 1 is a view in perspective of an instrument according to one aspect of the present invention.

Referring to FIG. 1, an instrument 100 employing an articulating image sensor assembly according to one aspect of the present invention includes an elongated shaft 101 and a handle 102. Shaft 101 extends from a proximal end shown generally at reference numeral 104 connected to handle 102 to a distal end generally indicated at reference numeral 105. A distal end portion 106 is included at the shaft distal end 105. The articulating image sensor assembly according to the present invention is located in distal end portion 106, although the assembly and the structure on which it is mounted are not shown in FIG. 1 due to the scale of the figure.

Instrument 100 receives electrical operating power through a cable 108 which extends from a proximal end of handle 102 in this example instrument. This power may be used to operate one or more light sources and other electronic elements mounted within distal end portion 106, such as an imaging device included in the image sensor assembly. Also, data signals from such an imaging device may be communicated through appropriate conduits within shaft 101 and handle 102 to cable 108. These data signals may be communicated through cable 108 to processing equipment (not shown) which processes the image data and drives one or more video monitors to display the images collected at distal end 105 of instrument 100. Those familiar with endoscopes and borescopes will appreciate that instrument 100 includes a number of additional features such as controls 110 for controlling the operation of the instrument. Although controls relating to the articulating image sensor assembly will be described further below, the general operation and control of instrument 100 will not be described further herein in order to avoid obscuring the present invention in unnecessary detail.

Figure 2:
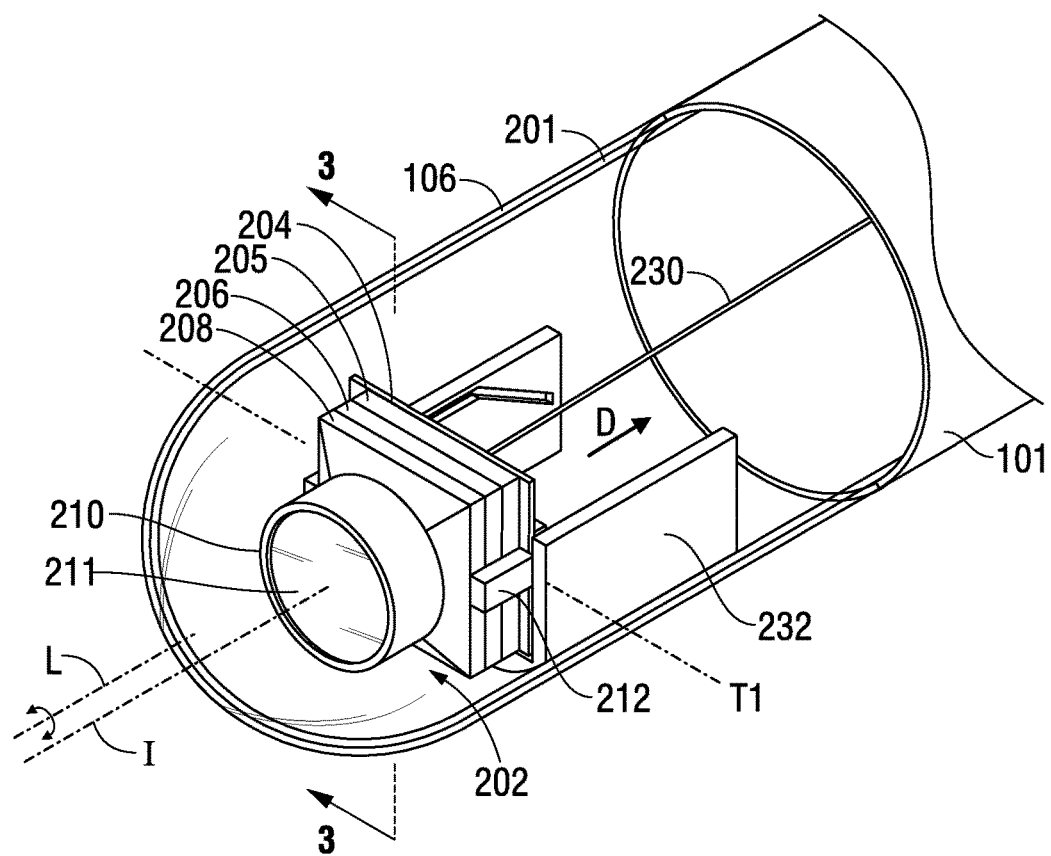
FIG. 2 is a view in perspective of the distal end of the instrument shaft shown in FIG. 1.

Referring to FIG. 2, it is apparent that distal end portion 106 of shaft 101 is transparent around its entire circumference. This particular embodiment includes an inner tube 201 that extends the entire length of instrument shaft 101 to handle 102 shown in FIG. 1. This inner tube 201 also includes a transparent end section and defines a first articulation structure in this embodiment of the invention, which, as will be described further below, allows the image sensor assembly shown generally at 202 to be rotated about the longitudinal L axis of shaft distal end portion 106.

Image sensor assembly 202 shown in FIGS. 2-6 includes a printed circuit board ("PCB") 204 on which is mounted an imaging device 205 which in this case may comprise, for example, a charge coupled device ("CCD") having a transparent cover 206. Image sensor assembly 202 also includes an adapter 208 which connects the rectangular image sensing device 205 and cover 206 to an objective lens assembly having a cylindrical sleeve 210. The objective lens assembly includes one or more lenses 211 mounted in sleeve 210 and allows image sensor assembly 202 to obtain an image within a field of view about an imaging axis I. The illustrated image sensor assembly also includes a light source in the form of two LED lamps 212 mounted on PCB 204. Image sensor assembly 202 is supported in inner tube 201 on two lateral side support structures, one on each lateral side of the image sensor assembly. In the embodiment shown in FIGS. 2-6 each lateral side support includes fore and aft projections, 214 and 215, respectively, on each lateral side of image sensor assembly 202 (as indicated particularly in FIGS. 3 and 4). These projections 214 and 215 cooperate with a track structure described below to facilitate articulation about a lateral articulation axis T1 shown in FIGS. 2 and 5.

Figure 3:
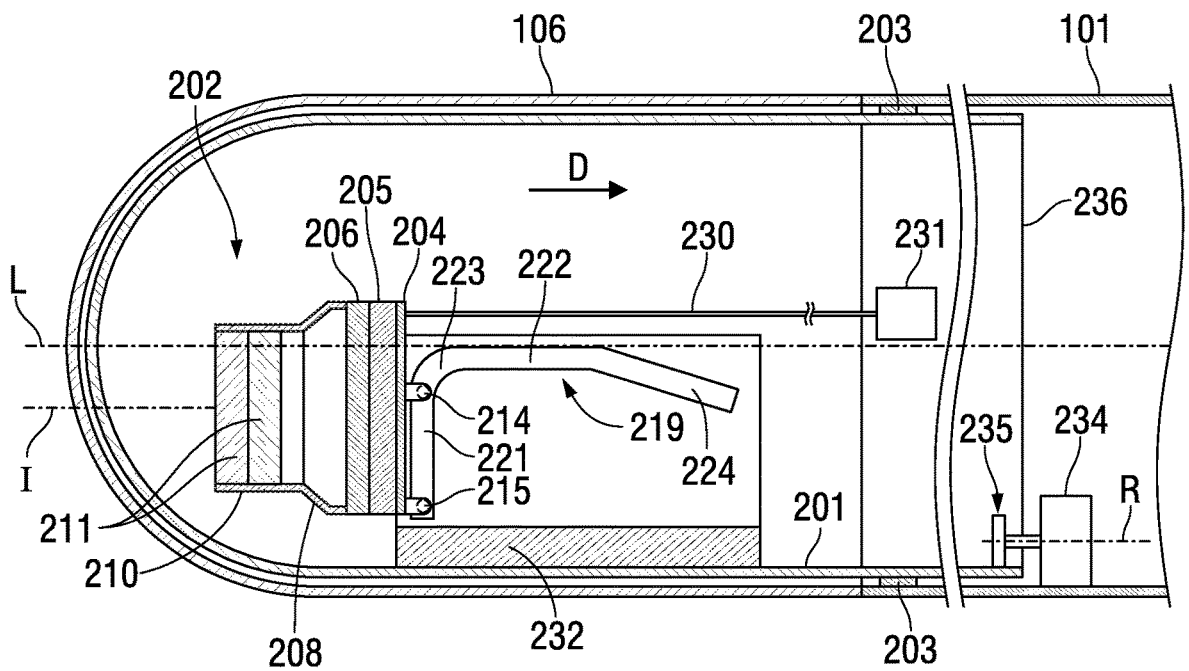
FIG. 3 view in section taken along line 3-3 in FIG. 2.

The articulating arrangement for the embodiment shown in FIGS. 2-6 includes the first articulating structure comprising inner tube 201 which is mounted for rotation within instrument shaft 101 and thus allows image sensor assembly 202 to be rotated about longitudinal axis L of shaft distal end portion 106. Suitable bearing material 203 may be positioned between inner tube 201 and shaft 101 at various points along the length of the inner tube to allow the inner tube to rotate smoothly within shaft 101. The articulating arrangement also includes a second articulating structure which is mounted on the first articulating structure comprising inner tube 201. The second articulating structure in this particular embodiment includes a respective track 218 and 219 on each lateral side of image sensor assembly 202. As shown in FIG. 3, track 219 includes a transverse section 221, a longitudinal section 222, a curved section 223 connecting the transverse and longitudinal sections, and an inclined section 224 at a bottom end of the longitudinal section. Track 218 includes a corresponding structure. The fore and aft projections 214 and 215 on each lateral side of image sensor assembly 202 are received in a respective one of the tracks 218, 219. As will be described further below, this arrangement of tracks 218 and 219 and first and second lateral side support structures comprising fore and aft projections 214 and 215 allows image sensor assembly 202 to be moved within the instrument distal end portion 106 so that the assembly pivots about the lateral articulation axis T1 shown in FIGS. 2 and 5.

It will be appreciated by those familiar with imaging devices (such as device 205 in FIGS. 2-6) that these devices may be accompanied by electronic components such as transistors, capacitors, resistors, and regulators for example. Additionally, imaging device 205 and its accompanying electronic components require electrical power and means for communicating image data to be processed for producing the collected images. The required operating power and data transmission may be provided through a suitable electrical cable. These accompanying electronic components and the power/data cable are omitted from the present drawings in order to more clearly illustrate the various features of the imaging apparatus. Those skilled in the art will appreciate that the electronic components and power/data cable may be connected to or included with image sensor assembly 202 in any number of fashions. For example, some embodiments of an articulating imaging apparatus according to the present invention may include the electronic components mounted on the side of PCB 204 opposite the side on which imaging device 205 is mounted. The power/data cable may also be connected to the back side of PCB 204 to provide operating power to image sensor assembly 202 and allow image data to be communicated from the image sensor assembly to processing equipment remote from the shaft distal end portion 106. However, the present invention is not limited to any particular mounting arrangement for electronic components which may accompany imaging device 205 and a power/data cable. Any accompanying electronic components and the power/data cable need only be mounted to provide the required function and allow the movement of image sensor assembly 202 across its desired range of movement.

Figure 6:
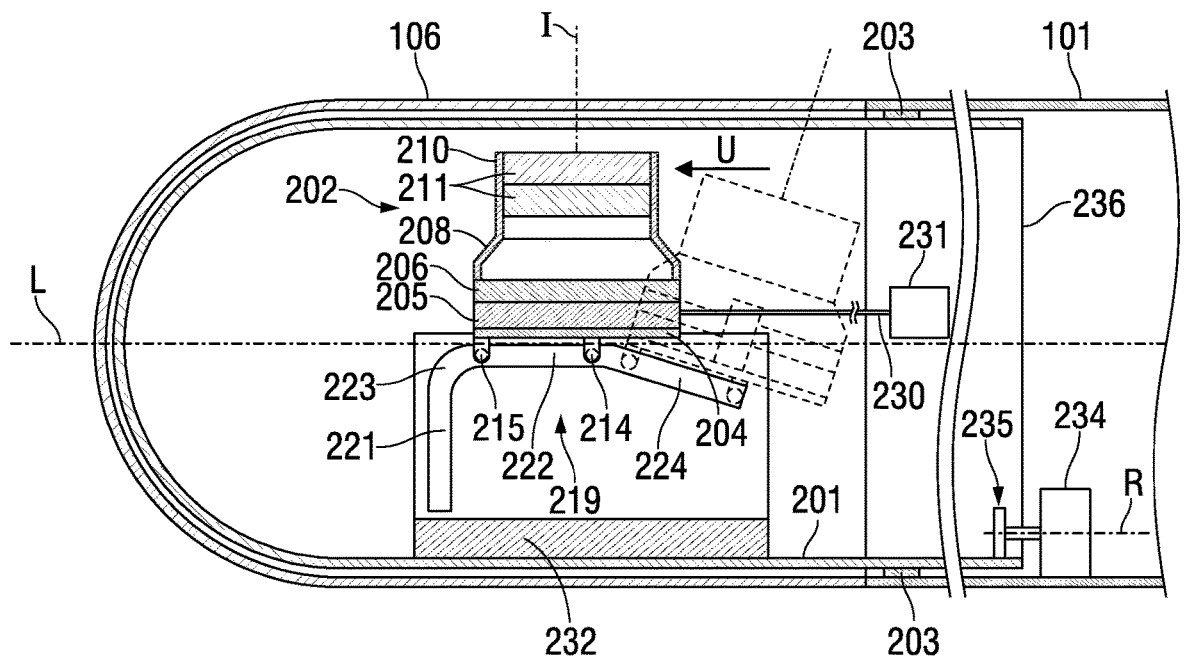
FIG. 6 is a view in section taken along line 6-6 in FIG. 5, and also showing an additional position of the image sensor assembly in phantom lines.

FIGS. 2, 3, 5, and 6 also show that image sensor assembly 202 is connected to a push wire 230 extending longitudinally along instrument shaft 101. Push wire 230 comprises part of an articulation control assembly in this embodiment of the invention and is used together with linear actuator 231 shown in FIGS. 3 and 6 to control the articulation of image sensor assembly 202 about lateral articulation axis T1 as will be described below. FIGS. 3 and 6 also show a motor 234 and drive linkage 235 which are also part of the articulation control assembly in this embodiment, and are used to control the articulation of image sensor assembly 202 about longitudinal axis L as will be described below.

FIGS. 2-6 may now be used to describe the articulation of image sensor assembly 202 within instrument distal end portion 106. In the position of image sensor assembly 202 shown in FIGS. 2-4, the image sensor assembly is oriented about lateral articulation axis T1 so that image sensing axis I is aligned essentially parallel to longitudinal axis L of shaft distal end portion 106. However, the present invention allows image sensor assembly 202 to be reoriented within shaft distal end portion 106 to change the field of view without moving the shaft distal end. In particular, from the position shown in FIGS. 2-4, image sensor assembly 202 may be moved to the position shown in FIGS. 5 and 6 in which image sensing axis I lies at an angle of approximately 90° to longitudinal axis L. It is the ability of the projections 214 and 215 to move along the tracks 218 and 219 which facilitates this lateral axis articulation in this embodiment of the invention. Push wire 230 may be manipulated longitudinally to place image sensor assembly 202 in the desired orientation about lateral articulation axis T1 within the instrument shaft distal end portion 106. As compared to the position shown best in FIGS. 2 and 3, push wire 230 may be pulled in the direction D in FIGS. 2 and 3 to move image sensor assembly 202 from the position shown in those figures to the position shown in FIGS. 5 and 6. Image sensor assembly 202 may be returned to the position shown in FIGS. 2-4 by moving push wire 230 in the opposite direction U shown in FIGS. 5 and 6. Of course image sensor assembly 202 may be stopped at any position between the position of FIG. 2 and the position of FIG. 5 in order to obtain a view at that particular location. Additionally, the inclined sections 224 of each track 218, 219 allow image sensor assembly 202 to be positioned as shown in phantom lines in FIG. 6 in which image sensing axis I extends somewhat back away from distal end portion 106 (for example, at an angle of 120° from longitudinal axis L. Also, since inner tube 201 is mounted for rotation about longitudinal axis L, image sensor assembly 202 (and its image sensing axis I) may be rotated to any position 360° around longitudinal axis L without changing the position of the instrument shaft. Thus the instrument operator is able to view a large area all without changing the position of the instrument relative to that area.

As shown in FIGS. 3 and 6 of the illustrated representative embodiment, linear actuator 231 controls push wire 230 and thus the position of image sensor assembly 202 along tracks 218, 219. Linear actuator 231 may comprise any suitable device for imparting the desired motion to push wire 230 and may be located at any point which does not interfere with the rotation of inner tube 201 about longitudinal axis L. FIGS. 3 and 6 also show motor 234 and drive linkage 235 which operate together to control the rotation of inner tube 201 about longitudinal axis L. Motor 234 may be any suitable device (such as a stepper motor) for rotating drive linkage 235 about its rotational axis R. Drive linkage 235 may rely on a frictional engagement with the inner surface of inner tube 201 or may cooperate with a gear (not shown) extending circumferentially around the inner surface of inner tube. Linear actuator 231 and motor 234 may be operated through controls located on handle 102 shown in FIG. 1. For example, one of the buttons shown at controls 110 in FIG. 1 may comprise a toggle button that may be depressed to one side to drive linear actuator 231 (and thus image sensor assembly 202) in one direction, and depressed to the opposite side to drive the linear actuator in the opposite direction. Similarly, another one of the buttons shown at controls 110 in FIG. 1 may comprise a toggle button that may be depressed to one side to drive motor 234 (and thus inner tube 201) in one rotational direction, and depressed to the opposite side to drive the motor in the opposite rotational direction. Of course, in the case of either linear actuator 231 or motor 234, the device will typically be associated with suitable control circuitry (not shown) which receives signals from the operator activated button or other control device as an input.

Figure 4:
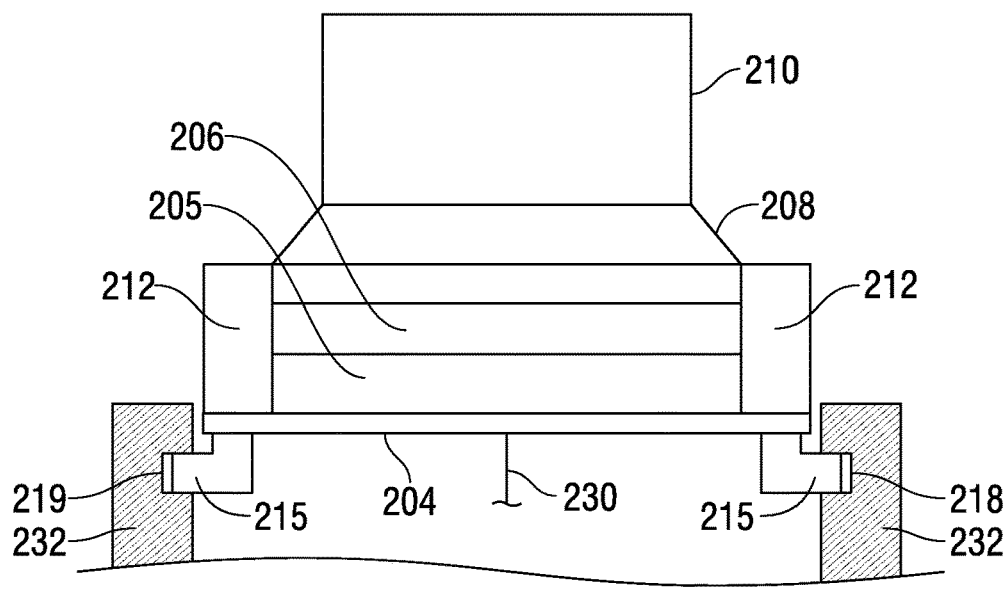
FIG. 4 is an end view of the image sensor assembly and a portion of the articulation track shown in FIG. 3.
Figure 5:
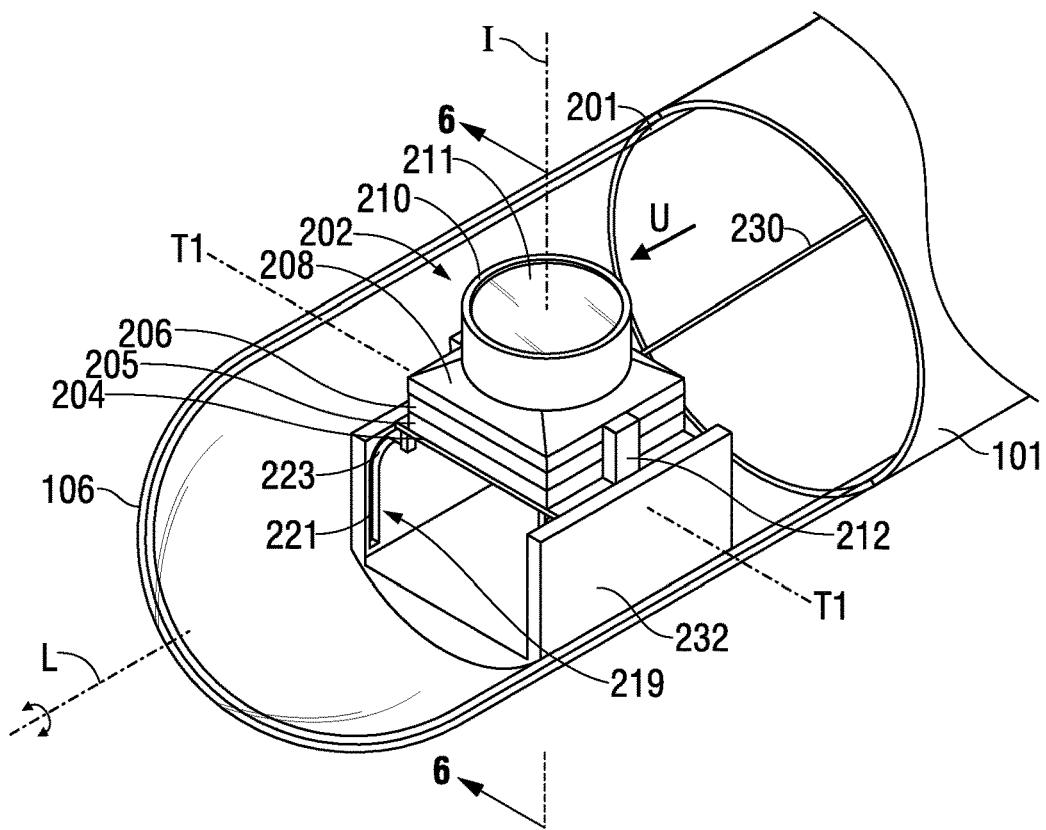
FIG. 5 is a view in perspective similar to FIG. 2 but showing the image sensor assembly rotated 90° about its lateral articulation axis.

FIG. 4 shows that tracks 218 and 219 forming the second articulating structure are mounted eccentrically within the inner tube 201. That is, tracks 218 and 219 are offset downwardly in the orientation of FIG. 3 from longitudinal axis L. This offset facilitates the lateral articulation (about axis T1) of image sensor assembly 202 within the confines of inner tube 201 and shaft distal end portion 106 in this embodiment of the invention. Without this offset, the end of lens assembly sleeve 210 would hit the inner surface of inner tube 201 as image sensor assembly 202 is articulated laterally from the position of FIG. 3, and this interference would not allow the image sensor assembly to reach the position shown in FIGS. 5 and 6. The offset of the second articulating arrangement comprising tracks 218 and 219 may be reduced or avoided by reducing the overall height and lateral dimensions of the image sensor assembly.

The position of the fore and aft projections 214 and 215 relative to image sensor assembly 202 also affects the ability to articulate image sensor assembly about lateral articulation axis T1. The example of FIGS. 2-4 shows the projections 214 and 215 to the right of the level of PCB 204 in the orientation of FIG. 3. It should be appreciated however that the distance from the projections 214 and 215 to the bottom of PCB 204 should be minimized in order to facilitate the lateral articulation of image sensor assembly 202 within the confines of inner tube 201 and shaft distal end portion 106. Other implementations may include the fore and aft projections 214 and 215 at the level of PCB 204 or even to the left of the level of the PCB in the orientation of FIG. 3.

It should also be noted that all of image sensor assembly 202 resides between tracks 218 and 219 to facilitate the desired movement along those tracks. This positioning of image sensor assembly 202 relative to tracks 218 and 219 facilitates movement of the assembly through certain intermediate positions between the position shown in FIG. 2 and the position shown in FIG. 5. Some of these intermediate positions, such as a position where image sensing axis extends at 45° to longitudinal axis L, place the plane of PCB 204 and other portions of image sensor assembly 202 within the area defined between tracks 218 and 219 and thus the PCB and at least those portions of the image sensor assembly must be configured to fit between the tracks in that situation.

In the embodiment shown in FIGS. 2-6, tracks 218 and 219 are formed in an insert 232 connected within inner tube 201. Insert 232 includes an exterior surface along one side which matches the curvature of the inner wall of tube 201. A suitable adhesive may be used to bond insert 232 in the desired position within tube 201. It should be appreciated that the insert 232 is shown only for example, and that the invention is not limited to that arrangement. Where tracks such as 218 and 219 are used in the second articulation structure, they can be formed and positioned in any suitable manner to provide the desired guide for projections 214 and 215.

Figure 7:
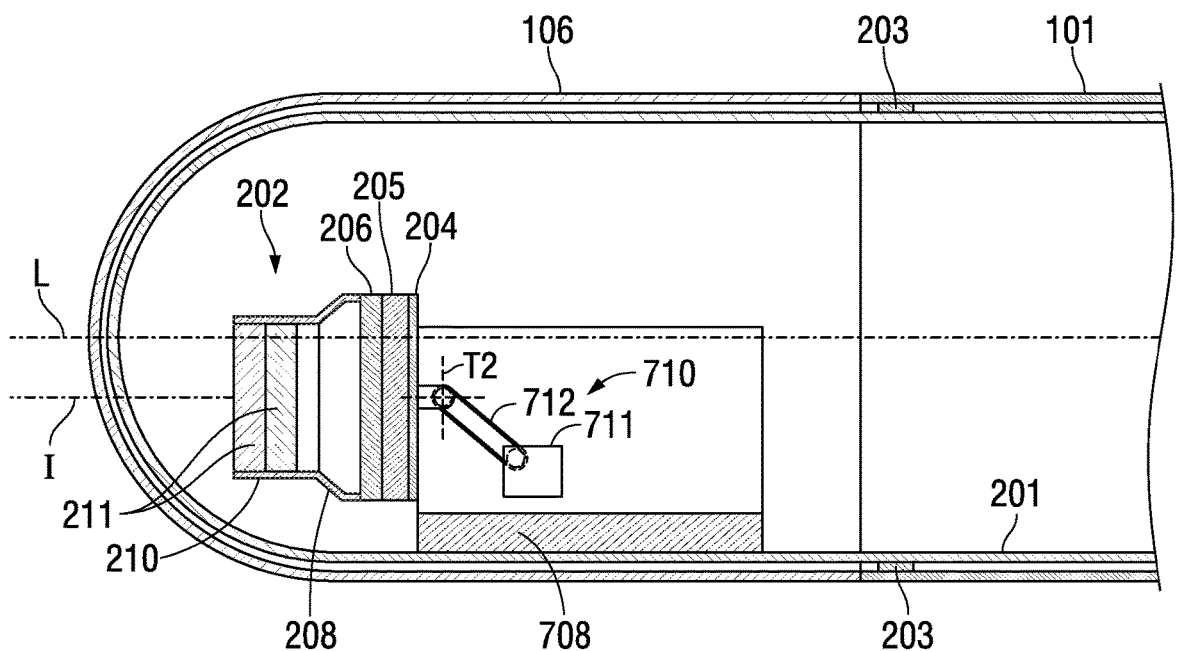
FIG. 7 is a view in section similar to FIG. 3 of an additional embodiment of the invention.
Figure 8:
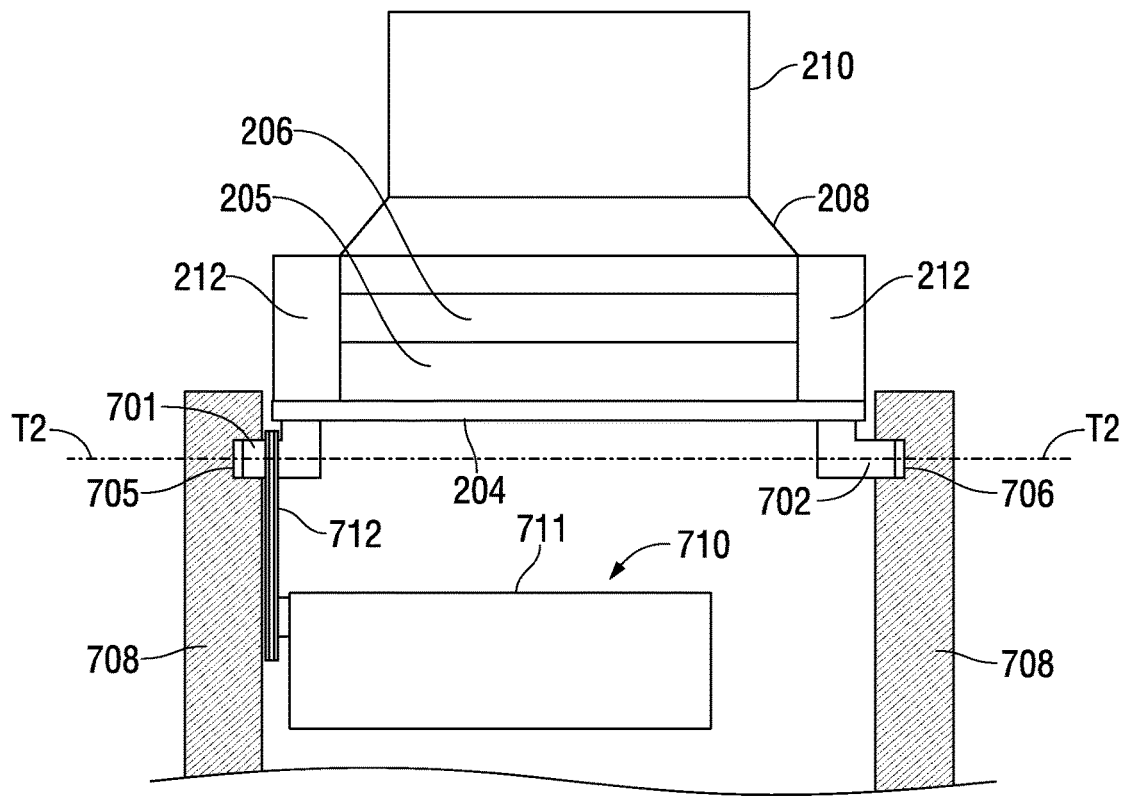
FIG. 8 is an end view of the image sensor assembly and pivot structure shown in FIG. 7.
Figure 9:
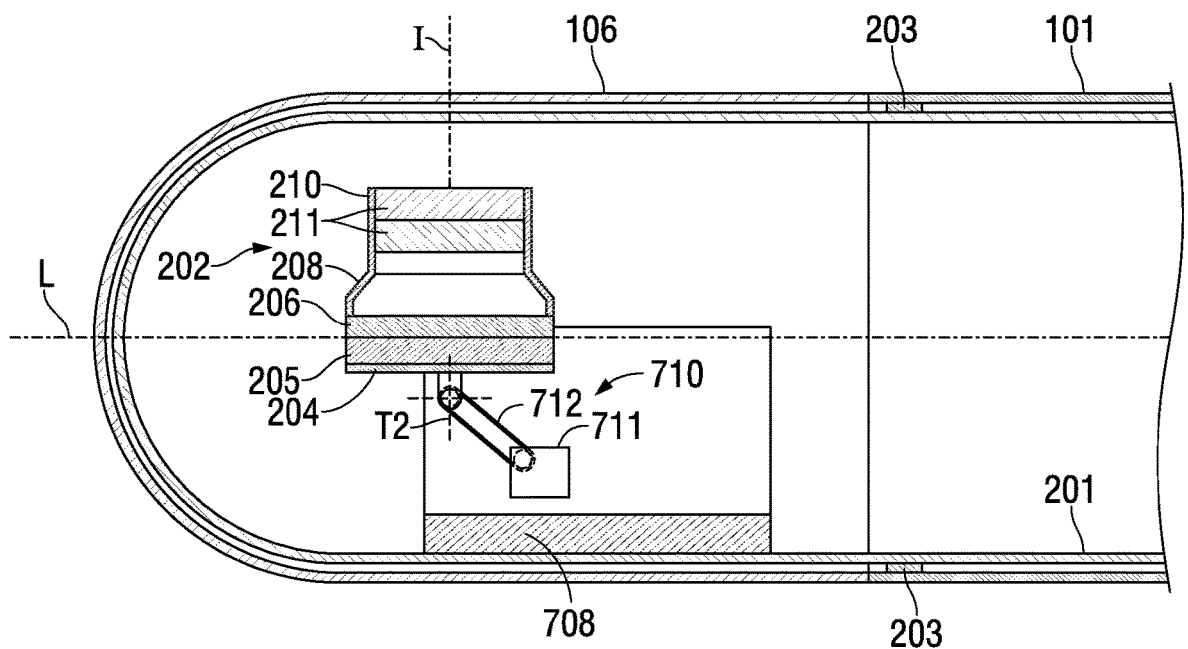
FIG. 9 is a view in section similar to FIG. 7, but showing the image sensor assembly rotated 90° about its lateral articulation axis.

FIGS. 7-9 show an alternative embodiment of an imaging device articulating arrangement according to the present invention with a different second articulating structure as compared to that shown in FIGS. 2-6. The embodiment shown in FIGS. 7-9 includes the same instrument shaft 101, shaft distal end portion 106, and inner tube 201 shown in the embodiment of FIGS. 2-6, as well as the same image sensor assembly 202. However, the second articulating structure in the embodiment of FIGS. 7-9 comprises a pivot structure which allows the image sensor assembly to be pivoted about a lateral articulation axis T2. In particular, this pivot arrangement includes a first lateral support structure on a first lateral side of image sensor assembly 202 comprising a first pivot element 701. A second lateral support structure on a second lateral side of image sensor assembly 202 comprises a second pivot element 702. These pivot elements 701 and 702 each comprise a respective projection aligned along lateral articulation axis T2. The second articulation structure in this alternative embodiment also includes first and second pivot bases 705 and 706 mounted on an insert 708 (similar to insert 232 in the embodiment of FIGS. 2-6) positioned in inner tube 201. These pivot bases 705 and 706 comprise receiving openings for receiving a respective one of the pivot projections 701 and 702. First projection 701 is received in first pivot base 705 and second projection 702 is received in second pivot base 706. This pivot structure allows image sensor assembly 202 to be pivoted about lateral articulation axis T2 from the orientation shown in FIGS. 7 and 8 to the orientation shown in FIG. 9 or any point in between. The pivot structure shown in FIGS. 7-9 also allows image sensor assembly 202 to be pivoted further than 90° to longitudinal axis L so that image sensing axis I is directed somewhat away from the distal end of the instrument and back toward the proximal end of shaft 101.

The orientation of image sensor assembly 202 in this illustrated example is controlled through an articulation control 710 comprising a motor 711 and sprocket or pulley system 712 operating between a shaft of motor 711 and pivot projection 701. Motor 711 may comprise any suitable device (such as a stepper motor) for imparting the desired rotation to image sensor assembly 202 and holding the assembly in a desired rotational position. Motor 711 may be controlled through a suitable motor control circuit (not shown) which takes an input from a control device on the instrument handle 102 shown in FIG. 1. Similarly to the previously described embodiment, a button included with controls 110 may comprise a toggle button which may be depressed to one side to drive motor 711 in one direction and depressed to the opposite side to drive the motor in the opposite rotational direction. Although not shown in FIGS. 7-9, rotation of inner tube 201 (and thus rotation of image sensor assembly 202 about longitudinal axis L) may be controlled via a motor and drive linkage similar to elements 234 and 235 shown in FIGS. 3 and 6.

FIGS. 7 and 9 show that lateral articulation axis T2 is offset from shaft distal end longitudinal axis L. Similarly to the offset of tracks 218 and 219 shown in FIG. 3, the offset of articulation axis T2 from longitudinal axis L allows image sensor assembly 202 to articulate at least 90° within the confines of inner tube 201. Also similarly to the previously described embodiment, projections 701 and 702 may be placed differently relative to the plane of the PCB for image sensor assembly 202. Rather than being located to the right of the PCB in the orientation of FIG. 7, projections 701 and 702 may be connected to the image sensor assembly so as to reside at the level of the PCB or to the left of that position in the orientation of FIG. 7.

The above-described embodiments are illustrated as having the lateral side support structures (fore and aft projections 214 and 215 in the embodiment of FIGS. 2-6, and pivot projections 701 and 702 in the embodiment of FIGS. 7-9) connected directly to the PCB 204 of image sensor assembly 202. Other forms of the invention may employ a separate tray (not shown) for supporting PCB 204, and the projections (214, 215 or 701, 702) may extend from the tray or from a side component connected to the tray. Alternatively from a tray that extends the width of PCB 204, separate side structures (not shown) may be adhered to each lateral side of the PCB and the projections (214, 215 or 701, 702) may extend from the respective side component. These tray and side component arrangements are useful to place the respective projections in the given embodiment to the left of the PCB 204 in the orientation of FIGS. 3 and 7.

Although electronic components such as transistors and capacitors accompanying image sensing device 205 may be positioned on the back side of PCB 204 opposite the side containing the image sensing device, other implementations may locate these electronic components differently. Other implementations may, for example, place the electronic components on an end of the power/data cable adjacent to PCB 204 or on an intermediate PCB (not shown) between the power/data cable and PCB.

Embodiments of the present invention may not include an inner tube such as tube 201 which extends all the way to the distal end of shaft 101. Rather, the inner tube in a given embodiment may extend only to a point within instrument shaft 101 to position the image sensor assembly 202 in the desired position within the transparent distal end portion 106 shown in the above-described figures. Also, even when the inner tube does extend the entire length of the instrument shaft, it need not be transparent around its entire circumference as shown in the present figures. The particular, the inner tube (such as tube 201 shown in the figures) may be transparent only at the end and along the side to which image sensor assembly 202 may be turned about the lateral articulating axis, so as not to block the field of view about the image sensing axis regardless of the orientation of the image sensor assembly about the lateral articulation axis.

In implementations employing an elongated tube for the first articulating structure, the tube may include a proximal end (236 in FIGS. 3 and 6) adapted to extend to a handle of the instrument when the imaging apparatus is mounted in the operating position in the instrument shaft. Thus the motor 234 may be mounted in handle 102 in FIG. 1. Otherwise the elongated inner tube 201 may not include a proximal end extending to the instrument handle, in which case either motor 234 may be mounted in the instrument shaft 101 to turn the tube about its longitudinal axis or a torque transmission element may extend from the elongated inner tube to the instrument handle for connection to a motor mounted in handle 102. It is also possible for a motor such as motor 234 to be replaced with a shaft that may be manually turned through a suitable linkage mounted on the instrument handle. Similarly, push wire 230 may be manipulated with a suitable manually operated control on the handle.

The various components of an articulating image sensing arrangement according to the present invention may be formed from any suitable material or combination of materials. The materials should be selected for compatibility with the instrument with which the apparatus is to be used, and the environments to which the instrument may be subjected. For example, for use in endoscopes, the components of the articulating image sensing arrangement should be compatible with materials and conditions used in sterilizing procedures for such endoscopes. Also, although a CCD-type imaging device is referenced in the representative examples described above, any suitable imaging device may be employed within the scope of the invention. For example, imaging device 205 may comprise a CMOS imaging device or any other type of imaging device.

It will be noted that in the embodiment shown in FIGS. 2-6, movement of image sensor assembly 202 from the transverse to longitudinal sections of tracks 218, 219 effects not only a pivoting movement of the image sensor assembly, but also a movement longitudinally along the instrument longitudinal axis L. Movement along the longitudinal sections and inclined sections of tracks 218, 219 similarly effects a longitudinal movement of image sensor assembly 202. The length of the longitudinal track sections 222 may be selected to provide the desired longitudinal range of motion for image sensor assembly 202. A similar longitudinal motion for the image sensing assembly 202 may be provided in the pivot-type structure shown in the embodiments of FIGS. 7-9 by mounting insert 708 for longitudinal movement within inner tube 201, or mounting at least the portion of insert 708 containing pivot bases 705 and 706 for such longitudinal movement. In either case, the movement may be effected by a suitable linear actuator (not shown) operatively coupled to insert 708 or that portion of the insert adapted to move longitudinally. This longitudinal movement arrangement combined with the pivoting movement of image sensor assembly 202 described in connection with FIGS. 7-9 provides a great deal of flexibility to the instrument operator to view various locations from different angles without having to move the instrument shaft adjacent to the area being viewed. Regardless of how the longitudinal movement of image sensor assembly is accomplished in a given implementation, the transparent shaft distal end portion 106 and transparent portions of inner tube 201 are preferably long enough to accommodate the entire range of longitudinal motion for the image sensor assembly 202 without blocking the field of view for the assembly.

It will be appreciated that the transparent sections of the instrument shaft distal end portion 106 and inner tube 201 may in some cases distort the image received by image sensing device 205. Embodiments of the present invention may be used with image processing systems which may compensate for any such image distortion.

As used herein, whether in the above description or the following claims, the terms "comprising," "including," "carrying," "having," "containing," "involving," and the like are to be understood to be open-ended, that is, to mean including but not limited to. Also, it should be understood that the terms "about," "substantially," and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Any use of ordinal terms such as "first," "second," "third," etc., in the following claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

In the above descriptions and the following claims, terms such as top, bottom, upper, lower, and the like with reference to a given feature are intended only to identify a given feature and distinguish that feature from other features. Unless specifically stated otherwise, such terms are not intended to convey any spatial or temporal relationship for the feature relative to any other feature.

The term "each" may be used in the following claims for convenience in describing characteristics or features of multiple elements, and any such use of the term "each" is in the inclusive sense unless specifically stated otherwise. For example, if a claim defines two or more elements as "each" having a characteristic or feature, the use of the term "each" is not intended to exclude from the claim scope a situation having a third one of the elements which does not have the defined characteristic or feature.

The above described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination.

The invention claimed is:

1. An instrument including:
    (a) an instrument shaft having a distal end portion which is transparent;
    (b) an image sensor assembly having an image sensing axis, a first lateral side, and a second lateral side;
    (c) a first articulating structure mounted at and enclosed within the distal end portion of the instrument shaft for rotation within the distal end portion of the instrument shaft about a longitudinal axis of the distal end portion of the instrument shaft;
    (d) a second articulating structure mounted on the first articulating structure eccentrically with respect to the longitudinal axis of the distal end portion of the instrument shaft;
    (e) a first lateral side support structure located at the first lateral side of the image sensor assembly;
    (f) a second lateral side support structure located at the second lateral side of the image sensor assembly, the first lateral side support structure and the second lateral side support structure each being mounted on the second articulating structure eccentrically with respect to the longitudinal axis of the distal end portion of the instrument shaft so as to position the image sensor assembly in the distal end portion of the instrument shaft and to facilitate articulation of the image sensor assembly so as to rotate the image sensing axis about a lateral articulation axis extending transverse to and offset from the longitudinal axis of the distal end portion of the instrument shaft; and
    (g) an articulation control assembly configured to control rotation of the first articulating structure about the longitudinal axis of the distal end portion of the instrument shaft and to control the articulation of the image sensor assembly about the lateral articulation axis.

2. The instrument of claim 1 wherein the first articulating structure includes a tube within the distal end portion of the instrument shaft with a longitudinal axis of the tube aligning with the longitudinal axis of the distal end portion of the instrument shaft, the tube being mounted within the instrument shaft for rotation about the tube longitudinal axis.

3. The instrument of claim 2 wherein the tube includes a distal end section which extends distally past the image sensor assembly in the instrument shaft, the distal end section of the tube including a transparent part over a field of view range for the image sensor assembly about the lateral articulation axis.

4. The instrument of claim 2 wherein the tube includes a proximal end which extends to a handle of the instrument.

5. The instrument of claim 1 further including one or more light sources mounted on the image sensor assembly.

6. The instrument of claim 1 wherein the second articulating structure facilitates movement of the image sensor assembly longitudinally along the distal end portion of the instrument shaft.

7. The instrument of claim 1 wherein:
(a) the first lateral side support structure includes a first side pivot element positioned at the first lateral side of the image sensor assembly;
(b) the second lateral side support structure includes a second side pivot element positioned at the second lateral side of the image sensor assembly aligned with the first side pivot element along the lateral articulation axis for the image sensor assembly; and
(c) the second articulating structure includes:
  (i) a first pivot base mounted on the first articulating structure and connected with the first side pivot element to allow rotation of the first side pivot element about the lateral articulation axis; and
  (ii) a second pivot base mounted on the first articulating structure and connected with the second side pivot element to allow rotation of the second side pivot element about the lateral articulation axis.

8. The instrument of claim 1 wherein:
(a) the first lateral side support structure includes fore and aft projections positioned at the first lateral side of the image sensor assembly so as to project past a plane aligned with and extending perpendicular to the first lateral side of the image sensor assembly;
(b) the second lateral side support structure includes fore and aft projections positioned at the second lateral side of the image sensor assembly so as to project past a plane aligned with and extending perpendicular to the second lateral side of the image sensor assembly;
(c) the fore and aft projections at the first lateral side of the image sensor assembly each align with the fore and aft projections at the second lateral side of the image sensor assembly along a respective fore and aft axis; and
(d) wherein the second articulating structure includes:
  (i) a first track mounted on the first articulating structure and configured to receive the fore and aft projections at the first lateral side of the image sensor assembly;
  (ii) a second track mounted on the first articulating structure and configured to receive the fore and aft projections at the second lateral side of the image sensor assembly; and
  (iii) the first and second track each include a transverse section, a longitudinal section, and a curved section connecting the transverse and longitudinal sections, the transverse sections extending transverse to the longitudinal axis of the distal end portion of the instrument, and the longitudinal sections extending parallel to the longitudinal axis of the instrument shaft distal end portion.

9. The instrument of claim 8 wherein the first and second track each include an inclined section at a bottom end of the respective longitudinal section, each inclined section being inclined so as to define a deviation greater than 90° with respect to the respective transverse section.

10. An imaging apparatus for an instrument having an elongated shaft with a transparent distal end portion, the imaging apparatus including:
(a) an image sensor assembly having an image sensing axis, a first lateral side, and a second lateral side;
(b) a first articulating structure mounted at and enclosed within the instrument shaft for rotation within the distal end portion of the instrument shaft about a longitudinal axis of the distal end portion of the instrument shaft when the imaging apparatus is in an operation position within the instrument shaft;
(c) a second articulating structure mounted on the first articulating structure eccentrically with respect to the longitudinal axis of the distal end portion of the instrument shaft when the imaging apparatus is in the operating position within the instrument shaft;
(d) a first lateral side support structure located at the first lateral side of the image sensor assembly; and
(e) a second lateral side support structure located at the second lateral side of the image sensor assembly, the first lateral side support structure and the second lateral side support structure each being mounted on the second articulating structure eccentrically with respect to the longitudinal axis of the distal end portion of the instrument shaft so as to position the image sensor assembly in the distal end portion of the instrument shaft and to facilitate articulation of the image sensor assembly so as to rotate the image sensing axis about a lateral articulation axis extending transverse to and offset from the longitudinal axis of the distal end portion of the instrument shaft when the imaging apparatus is mounted in the operating position in the instrument shaft.

11. The imaging apparatus of claim 10 wherein the first articulating structure includes a tube adapted to be positioned within the distal end portion of the instrument shaft with a longitudinal axis of the tube aligning with the longitudinal axis of the distal end portion of the instrument shaft.

12. The imaging apparatus of claim 11 wherein the tube includes a distal end section which is adapted to extend distally past the image sensor assembly in the instrument shaft when the imaging apparatus is mounted in the operating position in the instrument shaft, the distal end section of the tube including a transparent part over a field of view range for the image sensor assembly about the lateral articulation axis.

13. The imaging apparatus of claim 11 wherein the tube includes a proximal end adapted to extend to a handle of the instrument when the imaging apparatus is mounted in the operating position in the instrument shaft.

14. The imaging apparatus of claim 10 further including one or more light sources mounted on the image sensor assembly.

15. The imaging apparatus of claim 10 wherein the second articulating structure facilitates movement of the image sensor assembly longitudinally along the distal end portion of the instrument shaft when the imaging apparatus is in the operating position within the instrument shaft.

16. The imaging apparatus of claim 10 wherein:
(a) the first lateral side support structure includes a first side pivot element positioned at the first lateral side of the image sensor assembly;
(b) the second lateral side support structure includes a second side pivot element positioned at the second lateral side of the image sensor assembly aligned with the first side pivot element along the lateral articulation axis for the image sensor assembly; and
(c) the second articulating structure includes:

(i) a first pivot base mounted on the first articulating structure and connected with the first side pivot element to allow rotation of the first side pivot element about the lateral articulation axis; and
(ii) a second pivot base mounted on the first articulating structure and connected with the second side pivot element to allow rotation of the second side pivot element about the lateral articulation axis.

17. The imaging apparatus of claim 10 wherein:
(a) the first lateral side support structure includes fore and aft projections positioned at the first lateral side of the image sensor assembly so as to project past a plane aligned with and extending perpendicular to the first lateral side of the image sensor assembly;
(b) the second lateral side support structure includes fore and aft projections positioned at the second lateral side of the image sensor assembly so as to project past a plane aligned with and extending perpendicular to the second lateral side of the image sensor assembly;
(c) the fore and aft projections at the first lateral side of the image sensor assembly each align with the fore and aft projections at the second lateral side of the image sensor assembly along a respective fore and aft axis; and
(d) wherein the second articulating structure includes:
(i) a first track mounted on the first articulating structure and configured to receive the fore and aft projections at the first lateral side of the image sensor assembly;
(ii) a second track mounted on the first articulating structure and configured to receive the fore and aft projections at the second lateral side of the image sensor assembly; and
(iii) the first and second track each include a transverse section, a longitudinal section, and a curved section connecting the transverse and longitudinal sections, the transverse sections extending transverse to the longitudinal axis of the distal end portion of the instrument, and the longitudinal sections extending parallel to the longitudinal axis of the instrument shaft distal end portion.

18. The imaging apparatus of claim 17 wherein the first and second track each include an inclined section at a bottom end of the respective longitudinal section, each inclined section being inclined so as to define a deviation greater than 90° with respect to the respective transverse section.

* * * * *